(12) United States Patent
Flohr et al.

(10) Patent No.: US 7,501,406 B2
(45) Date of Patent: Mar. 10, 2009

(54) FLUORO SUBSTITUTED 2-OXO-AZEPAN DERIVATIVES

(75) Inventors: Alexander Flohr, Reinach (CH); Guido Galley, Rheinfelden (DE); Roland Jakob-Roetne, Inzlingen (DE); Eric Argirios Kitas, Aesch (CH); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 386 days.

(21) Appl. No.: 11/500,662

(22) Filed: Aug. 8, 2006

(65) Prior Publication Data

US 2007/0037789 A1 Feb. 15, 2007

(30) Foreign Application Priority Data

Aug. 12, 2005 (EP) .................................. 05107455

(51) Int. Cl.
*C07D 223/12* (2006.01)
*C07D 413/12* (2006.01)
*C07D 401/12* (2006.01)
*A61K 31/55* (2006.01)

(52) U.S. Cl. ........................... 514/212.03; 514/212.08; 540/524; 540/527

(58) Field of Classification Search ................. 540/524, 540/527; 514/212.03, 212.08
See application file for complete search history.

(56) References Cited

FOREIGN PATENT DOCUMENTS

WO WO 2004/084898 A1 10/2004
WO WO 2005/042489 A1 5/2005

OTHER PUBLICATIONS

Haass, C., The EMBO Journal (2004), vol. 23, pp. 483-488.
Fraering et al., Biochemistry (2004), vol. 43(30), pp. 9774-9789.
Sisodia et al., Nature Reviews/ Neuroscience, vol. 3, Apr. 2002, pp. 281-290.
Beher et al., Biochemical Society Transactions (2002), vol. 30, Part 4, pp. 534-537.
Wolfe, M. S., Current Topics in Medicinal Chemistry, (2002), vol. 2, pp. 371-383.
Tsai et al., Current Medicinal Chemistry, (2002), vol. 9, No. 11, pp. 1087-1106.
Sambamurti et al., Drug Development Research, vol. 56, (2002) pp. 211-227.
May, P. C., Drug Discovery Today, vol. 6, (2001), No. 9, pp. 459-462.
Nunan et al., FEBS Letters, vol. 483 (2000) pp. 6-10.
Hardy et al., Science, vol. 297, (2002) pp. 353-356.
Wolfe, M. S., Journ. of Medicinal Chemistry, vol. 44, No. 13, (2001) pp. 2039-2060.
Herreman et al., Nature Cell Biology (2000), vol. 2, pp. 461-462.
De Strooper et al., Nature, vol. 398, (1999) pp. 518-522.
Chung et al., Nature Cell Biology, (2001) vol. 3, pp. 1129-1132.
Hadland et al., PNAS vol. 98 (2001), pp. 7487-7491.
Ferrando et al., Cancer Cell, vol. 1 (2002) pp. 75-87.
Weng et al., Science, vol. 306, (2004) pp. 269-271.
Weng et al., Mol. Cell Biol. vol. 23, (2003) pp. 655-664.
Weijzen et al., Nature Medicine vol. 8, (2002) pp. 979-986.
Nickoloff et al., Oncogene vol. 22 (2003) pp. 6598-6608.
Li, et al., PNAS vol. 97(11) (2000) pp. 6138-6143.
Brockhaus et al., Neuroreport vol. 9(7) (1998) pp. 1481-1486.

*Primary Examiner*—Bruck Kifle
(74) *Attorney, Agent, or Firm*—George W. Johnston; Patricia S. Rocha-Tramaloni; Kimberly J. Prior

(57) ABSTRACT

The invention relates to compounds of general formula

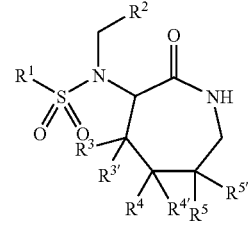

I wherein
$R^1$,
$R^2$,
$R^3/R^{3'}$, $R^4/R^{4'}$ and $R^5/R^{5'}$ are as defined in the specification and to pharmaceutically acceptable acid addition salts, optically pure enantiomers, racemates or diastereomeric mixtures thereof. The compounds are γ-secretase inhibitors which can be useful in the treatment of Alzheimer's disease or common cancers including, but not limited to, cervical carcinomas and breast carcinomas and malignancies of the hematopoietic system.

13 Claims, No Drawings

FLUORO SUBSTITUTED 2-OXO-AZEPAN DERIVATIVES

PRIORITY TO RELATED APPLICATIONS

This application claims the benefit of European Application No. 05107455.7, filed Aug. 12, 2005, which is hereby incorporated by reference in its entirety.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. The latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be presenilin, nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch. It was demonstrated by genetic means, i.e., ablation of either the presenilin 1 and 2 genes or the nicastrin gene, that γ-secretase is absolutely required for Notch signaling. This was subsequently confirmed by treatment with specific γ-secretase inhibitors.

Notch receptors are not only essential in embryonal development but also play a critical role in several tissues of the adult organism which continue to undergo proliferation and differentiation, e.g., hematopoietic cells and epithelia of the gut and skin. The signaling of Notch receptors occurs through an ordered sequence of events: binding to a ligand of the Delta or Jagged group, cleavage of the extracellular domain by an ADAM protease (TACE) and subsequent cleavage by the γ-secretase within the Notch transmembrane domain. The latter cleavage results in the liberation of the cytoplasmic domain which then translocates to the nucleus where it acts with other proteins as a regulator of a specific group of genes. A role for Notch in human oncogenesis was most clearly established for T-cell Acute Lymphoblastic Leukemia (T-ALL). Some rare cases of T-ALL show a (7:9) chromosomal translocation which leads to a constitutive activation of Notch1. Recently it was reported that ca. 50% of all T-ALL cases have point mutation in the Notch1 receptor which also cause over-activation. It was shown that growth of some cell lines derived from such leukemias were sensitive to treatment with γ-secretase inhibitors which confirmed an essential role for Notch1 signaling.

A broader role for Notch in oncogenesis is discussed in several recent paper which describe that its signaling is required for maintaining the neoplastic phenotype in ras-transformed cells. Deregulation of the ras-signaling pathway is found in a number of common cancers including cervical carcinomas and breast carcinomas.

The γ-secretase activity is absolutely required for the production of Abeta peptides. This has been shown both by genetic means, i.e., ablation of the presenilin genes and by low-molecular-weight inhibitory compounds. Since according to the amyloid hypothesis of AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:

The EMBO Journal (2204), 23, 483-488,
Biochemistry (2004), 43 (30), 9774-9789,
Nature Reviews/Neuroscience, Vol. 3, April 2002/281,
Biochemical Society Transactions (2002), Vol. 30. part 4,
Current Topics in Medicinal Chemistry, 2002, 2, 371-383,
Current Medicinal Chemistry, 2002, Vol. 9, No. 11, 1087-1106,
Drug Development Research, 56, 211-227, 2002,
Drug Discovery Today, Vol. 6, No. 9, May 2001, 459-462,
FEBS Letters, 483, (2000), 6-10,
Science, Vol. 297, 353-356, July 2002,
Journ. of Medicinal Chemistry, Vol. 44, No. 13, 2001, 2039-2060,
Nature Cell Biology 2, 461-462, 2000,
Nature 398, 518-522, 1999,
Nature Cell Biology 3, 1129-1132, 2001,
PNAS 98, 7487-7491, 2001,
Cancer Cell 1, 75-87, 2002,
Science 306, 269-271, 2004,
Mol Cell Biol 23, 655-664, 2003,
Nature Medicine 8, 979-986, 2002 and
Oncogene 22, 6598-6608, 2003.

SUMMARY OF THE INVENTION

The invention provides compounds of formula

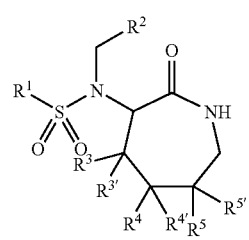

I wherein

R[1] is lower alkyl substituted by halogen, or is aryl or heteroaryl each of which is unsubstituted or substituted by halogen;

R[2] is heterocycloalkyl, aryl or heteroaryl, each of which is unsubstituted or substituted by one or more substituents selected from the group consisting of halogen, lower alkyloxy, lower alkyl substituted by halogen, O-lower alkyl substituted by halogen, C(O)—NR"$_2$, (CR$_2$)$_m$—C(O)—R', heteroaryl and S(O)$_2$-lower alkyl;

R[3]/R[3'], R[4]/R[4'] and R[5]/R[5'] are each independently hydrogen or fluoro, wherein at least one of R[4]/R[4'] or R[5]/R[5'] is always fluoro;

R' is aryl or hydroxy;

R" is hydrogen, cycloalkyl or heterocycloalkyl;

R is hydrogen or lower alkyl; and m is 0, 1, 2 or 3;

and pharmaceutically acceptable acid addition salts, optically pure enantiomers, racemates or diastereomeric mixtures thereof.

The invention also provides pharmaceutical compositions containing a therapeutically effective amount of one or more compounds of the invention and a pharmaceutically acceptable carrier. The invention further provides methods for the production of the compounds and compositions of the invention.

Compounds of formula I and related compounds of the invention are γ-secretase inhibitors thereby reducing reducing or preventing the formation of the various amyloidogenic Abeta peptides. Furthermore, compounds of the invention can block the Notch signaling pathways. Compounds of the invention can be used for the control or prevention of diseases related to the γ-secretase inhibition. The invention provides methods for the treatment of Alzheimer's disease and common cancers including, but not limited to, cervical carcinomas and breast carcinomas and malignancies of the hematopoietic system. Such methods comprise administering a therapeutically effective amount of a compound of the invention.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "lower alkoxy" denotes a group wherein the alkyl residue is as defined above, which is attached via an oxygen atom.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, for example phenyl or naphthyl. The preferred aryl group is phenyl.

The term "heteroaryl" denotes a monovalent aromatic carbocyclic radical, containing at least one heteroatom, selected from the group consisting of N, O or S, for example pyridyl, pyrazinyl, pyrimidinyl, pyridazinyl, triazinyl, thiazolyl, thienyl, furyl, pyrrolyl, imidazolyl, pyrazolyl, isothiazolyl, tetrazoly, [1,2,4]triazolyl, [1,2,4]oxidiazolyl, oxazolyl, or isoxazolyl, Preferred heteroaryl groups are pyridyl, thienyl, triazinyl, furyl or thiazolyl.

The term "heterocycloalkyl" denotes a non aromatic hydrocarbon radical containing at least one heteroatom, selected from the group consisting of N, O or S, for example oxetanyl, tetrahydrofuranyl, tetrahydropyranyl, azetidinyl, pyrrolidinyl, piperidinyl, piperazinyl, morpholinyl or thiomorpholinyl. Preferred heterocycloalkyl groups are morpholinyl, piperidinyl or pyrrolidinyl.

The term "cycloalkyl" denotes a saturated carbocyclic ring, containing 3-7 carbon atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The invention provides compounds of formula

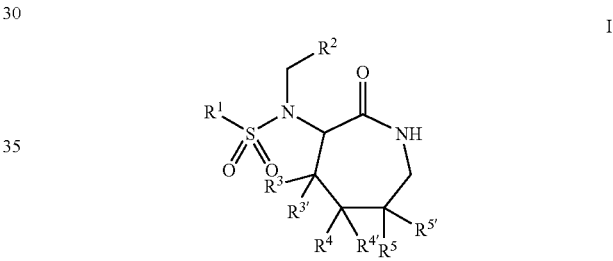

wherein

R[1] is lower alkyl substituted by halogen, or is aryl or heteroaryl each of which is unsubstituted or substituted by halogen;

R[2] is heterocycloalkyl, aryl or heteroaryl, each of which is unsubstituted or substituted by one or more substituents selected from the group consisting of halogen, lower alkyloxy, lower alkyl substituted by halogen, O-lower alkyl substituted by halogen, C(O)—NR"$_2$, (CR$_2$)$_m$—C(O)—R', heteroaryl and S(O)$_2$-lower alkyl;

R[3]/R[3'], R[4]/R[4'] and R[5]/R[5'] are each independently hydrogen or fluoro, wherein at least one of R[4]/R[4'] or R[5]/R[5'] is always fluoro;

R' is aryl or hydroxy;

R" is hydrogen, cycloalkyl or heterocycloalkyl;

R is hydrogen or lower alkyl; and m is 0, 1, 2 or 3;

and pharmaceutically acceptable acid addition salts, optically pure enantiomers, racemates or diastereomeric mixtures thereof.

The most preferred compounds of formula I are those, wherein

R[4]/R[4'] are both fluoro and R[1] is phenyl substituted by halogen.

Preferred compounds from this group are further those, wherein $R^2$ is phenyl substituted by halogen and/or $C(O)$—$N(R'')_2$, for example the following compounds 4-{[(4-chloro-benzenesulfonyl)-((R)-5,5-difluoro-2-oxo-azepan-3-yl)-amino]-methyl}-N-cyclopropyl-benzamide and 4-{[(4-chloro-benzenesulfonyl)-((R)-5,5-difluoro-2-oxo-azepan-3-yl)-amino]-methyl}-3-fluoro-N-pyrrolidin-1-yl-benzamide.

Further preferred compounds from this group are those, wherein $R^2$ is phenyl, substituted by halogen or lower alkoxy, for example the compound 4-chloro-N-(2,3-difluoro-4-methoxy-benzyl)-N-((R)-5,5-difluoro-2-oxo-azepan-3-yl)-benzenesulfonamide.

Preferred compounds from this group are those, wherein $R^2$ is phenyl, substituted by halogen or heteroaryl, for example the following compound 4-chloro-N-((R)-5,5-difluoro-2-oxo-azepan-3-yl)-N-[2-fluoro-4-(2H-[1,2,4]trialzol-3-yl)-benzyl]-benzenesulfonamide.

Preferred compounds from this group are further those, wherein $R^2$ is phenyl substituted by $(CR_2)_mC(O)$—R', for example the following compounds 3(4-{[(4-chloro-benzenesulfonyl)-((R)-5,5-difluoro-2oxo-azepan-3yl)-amino]methyl}-phenyl)-propionic acid and 3-(4-{[(4-chloro-benzenesulfonyl)-((R)-5,5-difluoro-2-oxo-azepan-3-yl)-amimo]-methyl}-phenyl)-3-methyl-butyric acid.

Preferred compounds are further those, wherein $R^1$ is heteroaryl substituted by halogen or $R^1$ is lower alkyl substituted by halogen.

The present compounds of formula I and their pharmaceutically acceptable salts can be prepared by methods known in the art, for example, by processes described below, which processes comprise a) reacting a compound of formula

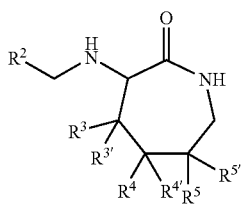

II with a compound of formula

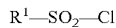    III $R^1$—$SO_2$—Cl to obtain a compound of formula

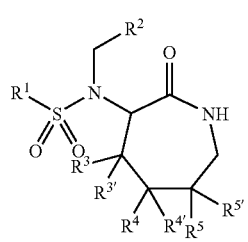

I wherein $R^1$, $R^2$, $R^3/R^{3'}$, $R^4/R^{4'}$ and $R^5/R^{5'}$ have the meaning as described above, or b) reacting a compound of formula

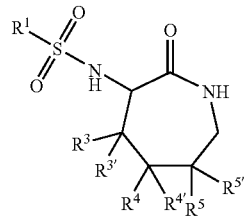

IV with a compound of formula $R^2$—$CH_2$-hal    V in the presence of a base or with a compound of formula $R^2$—$CH_2$—OH    VI in the presence of $Ph_3P$ and DIAD to obtain a compound of formula

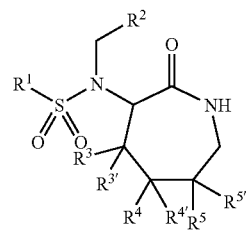

I wherein $R^1$, $R^2$, $R^3/R^{3'}$, $R^4/R^{4'}$ and $R^5/R^{5'}$ have the meaning as described above, and if desired, converting the compounds obtained into pharmaceutically acceptable acid addition salts.

The detailed processes for preparing of compounds of formula I are described in schemes 1 and 2 and in Examples 1-18. The starting materials of formulae III, V, VI, VII, VIII, IX, X and XI are known compounds or can be prepared by methods well-known in the art.

The following abbreviations have been used:

DIAD—diethylazodicarboxylate

DMAP—4-dimethylaminopyridine

EDC—1-ethyl-3-(3-dimethylaminopropyl)carbodiimide

TATU—1,1,3,3-tetramethyl-2-(1H-1,2,3-triazolo[5,4-b]pyridine-1-yl)-uronium tetrafluoroborate TPTU—O-(1,2-dihydro-2-oxo-1-pyridyl)-N,N,N',N'-tetramethyluronium tetrafluoroborate DMB—2,4-dimethoxybenzyl DAST—diethylaminosulfur trifluoride DMF—N,N-dimethylformamide Deoxofluor—[bis(2-methoxy-ethyl)amino]sulfur trifluoride Scheme 1

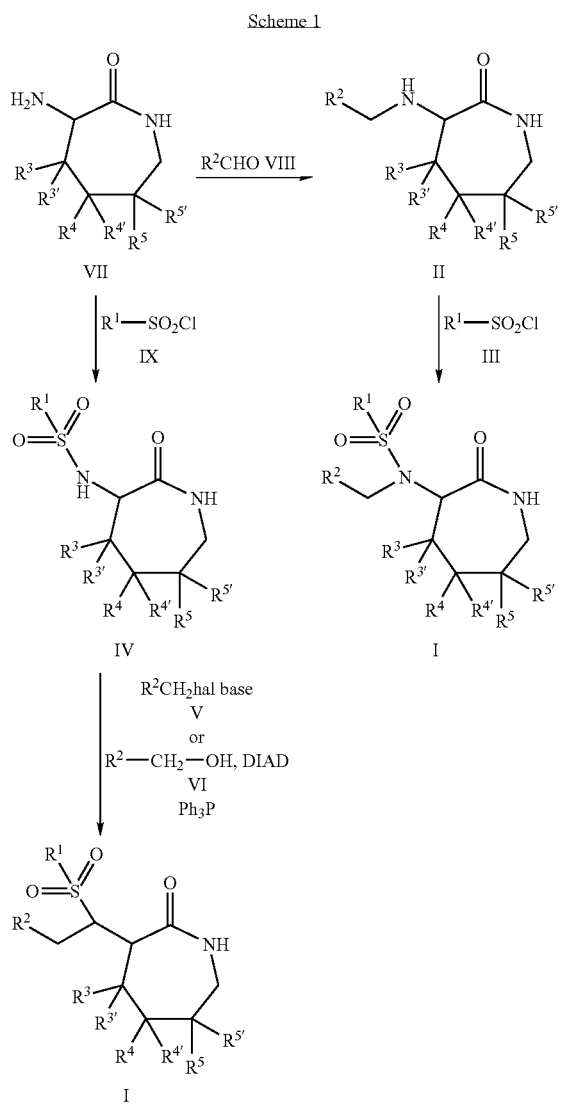

wherein $R^1$, $R^2$, $R^3/R^{3'}$, $R^4/R^{4'}$ and $R^5/R^{5'}$ have the meaning as described above and $Ph_3P$ is triphenylphosphine.

An amino-azepan-2-one of formula VII is treated with an aldehyde and a suitable reducing reagent, such as sodium triacetoxyborohydride or sodium cyanoborohydride, to yield an amine compound of formula II. A solution of this amine in dichloromethane can be reacted with one equivalent of an aromatic sulfonyl chloride in the presence of a base, such as Hünig's base or triethylamine, and catalytic DMAP to yield after column chromatography a pure compound of formula I. Alternatively, the compound of formula VII can be reacted first with the sulfonyl chloride, resulting in sulfonamide compounds of formula IV, which are amenable to further derivatization using for example a Mitsunobu protocol whereby an alcohol $R_2CH_2OH$, triphenylphosphine and diisopropyl or diethyl azodicarboxylate are reacted at low temperature under an inert atmosphere in a dry solvent such as tetrahydrofuran. The reaction mixture is allowed to warm up and further stirred at room temperature for several hours to furnish after column chromatography compounds of formula I. Intermediates of formula IV can also be used in a reaction where a halide $R^2CH_2$hal in the presence of excess potassium carbonate, catalytic potassium iodide in dry DMF solvent and at an elevated temperature are reacted. The reaction mixture is then filtered, acidified and purified using column chromatography to give compounds of formula I.

Fluoro ring-substituted 3-amino-azepan-2-ones of formula VII can be prepared by various methods described in the literature and specifically by one approach outlined in Scheme 2.

Scheme 2

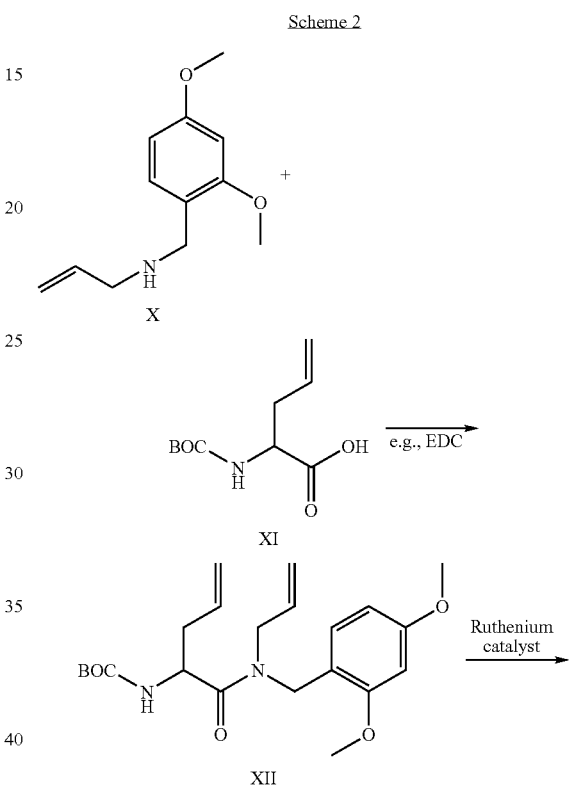

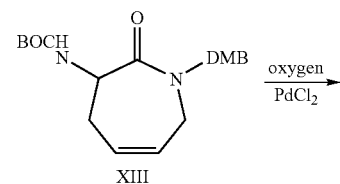

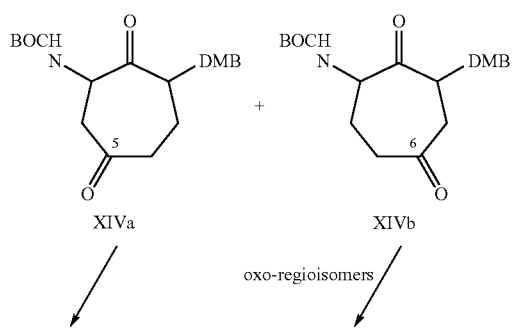

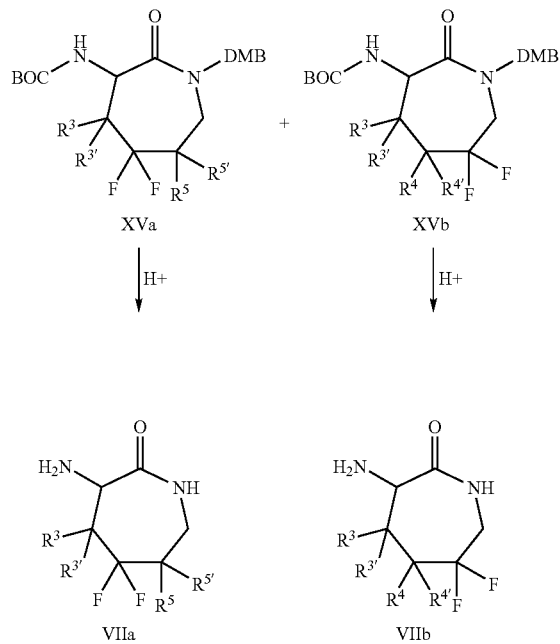

An amine of formula X (which is accessible by reacting the substituted benzaldehyde with allylamines under reductive conditions) can be coupled to an amino acid derivative of formula XI using standard peptide coupling reagents such as EDC or TATU to afford in high yields, bis-allyl derivatives of formula XII. Ring closure metathesis of compounds of formula XII can be achieved using ruthenium based catalysts such as those described by Grubbs. The $2^{nd}$ generation Grubbs catalyst was most efficient to prepare compounds of formula XIII. The resultant alkenes of formula XIII can be oxidized to the 5,6-oxo regioisomers of formula XIV via palladium complexes in a saturated oxygen environment. The regioisomeric mixture of ketones with formula XIV are not easily separated by chromatography. This mixture can be further transformed to geminal difluorinated compounds of formula XV using commercial reagents such as DAST or Deoxofluor. Compounds of formula XV can be adequately separated by silica gel chromatography. Protecting group removal under acidolytic conditions will furnish fluoro ring-substituted 3-amino-azepan-2-ones of formula VII.

The detailed description can be found in Examples A-K and 1-18.

If compounds of Formula I are basic, they can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acids, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable addition salts possess valuable pharmacological properties. Specifically, compounds of the present invention may inhibit γ-secretase.

The compounds were investigated in accordance with the test given hereinafter.

Description of γ-secretase Assay

The activity of test compounds can be evaluated in assays which measure the proteolytic cleavage of suitable substrates by γ-secretase activity. These can be cellular assays where e.g., a substrate of γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. The latter consists of the C-terminal 100 amino acids of human APP fused to a 6×Histidin tail for purification which is expressed in *E. coli* in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138-6143 (2000). Hek293 cells are mechanically disrupted, and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481-1486 (1998).

The preferred compounds show a $IC_{50}<10$ nM. In the list below are described some data to the γ-secretase inhibition:

I

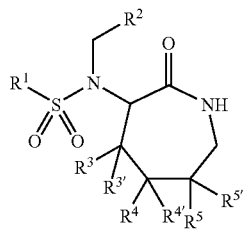

| R¹ | R² | R³/R³' | R⁴/R⁴' | R⁵/R⁵' | IC$_{50}$ nM | Example |
|---|---|---|---|---|---|---|
| 4-Cl-C₆H₄ | 4-(cyclopropylaminocarbonyl)phenyl | H/H | F/F | H/H | 4 | 1 (R) |
| 4-Cl-C₆H₄ | 4-(isoxazol-5-yl)phenyl | H/H | F/F | H/H | 19 | 2 (R) |
| 4-Cl-C₆H₄ | 6-methoxypyridin-3-yl | H/H | F/F | H/H | 29 | 3 (R) |
| 4-Cl-C₆H₄ | 2,3-difluoro-4-methoxyphenyl | H/H | F/F | H/H | 2 | 4 (R) |
| 4-Cl-C₆H₄ | 2-fluoro-4-methoxyphenyl | H/H | F/F | H/H | 17 | 5 (R) |
| 4-Cl-C₆H₄ | 3-fluoro-4-carboxyphenyl | H/H | F/F | H/H | 41 | 6 (R) |
| 4-Cl-C₆H₄ | 3-fluoro-4-(pyrrolidin-1-ylaminocarbonyl)phenyl | H/H | F/F | H/H | 7 | 7 (R) |
| 4-Cl-C₆H₄ | 4-(methylsulfonyl)phenyl | H/H | F/F | H/H | 17 | 8 (R) |
| 4-Cl-C₆H₄ | 4-(difluoromethoxy)phenyl | H/H | F/F | H/H | 45 | 9 (R) |

-continued

I

| R¹ | R² | R³/R³' | R⁴/R⁴' | R⁵/R⁵' | IC₅₀ nM | Example |
|---|---|---|---|---|---|---|
| 4-Cl-phenyl | 4-(CHF₂)-phenyl | H/H | F/F | H/H | 20 | 10 (R) |
| 4-Cl-phenyl | 4-(N-benzoyl-piperidin-4-yl)-phenyl | H/H | F/F | H/H | 460 | 11 (R) |
| 4-Cl-phenyl | 3-fluoro-4-(1H-1,2,4-triazol-3-yl)phenyl | H/H | F/F | H/H | 6 | 12 (R) |
| 4-Cl-phenyl | 4-(N-cyclopropylcarbamoyl)phenyl | H/H | H/H | F/F | 297 | 13 (R) |
| 4-Cl-phenyl | 4-(2-carboxyethyl)phenyl | H/H | F/F | H/H | 5 | 14 (R) |
| 4-Cl-phenyl | 4-(2-carboxy-1,1-dimethylethyl)phenyl | H/H | F/F | H/H | 10 | 15 (R) |
| 3,3,3-trifluoropropyl | 6-methoxypyridin-3-yl | H/H | F/F | H/H | 150 | 16 (R) |
| 5-chlorothiophen-2-yl | 6-methoxypyridin-3-yl | H/H | F/F | H/H | 110 | 17 (R) |
| 5-chloropyridin-2-yl | 4-(OCHF₂)-phenyl | H/H | F/F | H/H | 1000 | 18 (R) |

The present invention also provides pharmaceutical compositions containing compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

In addition, the pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of the invention and, if desired, one or more other therapeutically valuable substances into a galenical administration form together with one or more therapeutically inert carriers.

The compounds and compositions of the invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions or suspensions. The pharmaceutical compositions also can be administered rectally, for example, in the form of suppositories, or parenterally, in the form of injectable solutions.

In accordance with the invention compounds of formula I as well as their pharmaceutically acceptable salts are useful in the control or prevention of illnesses based on the inhibition of γ-secretase, such as of Alzheimer's disease. The compounds also are useful for the treatment of cancers including, but not limited to, cervical carcinomas and breast carcinomas and malignancies of the hematopoietic system.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLE A

4-Chloromethyl-N-cyclopropyl-benzamide

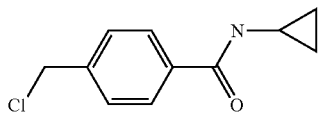

4-Chloromethyl-benzoyl chloride (2.82 g, 15 mmol) and cyclopropylamine (1.26 ml, 18 mmol) were reacted in $CH_2Cl_2$ (30 ml) and in the presence of Hünig's base (3.1 ml, 18 mmol) for 1 h. A precipitate was formed which was resolubilized by adding ethyl acetate. The reaction mixture was washed with a 5% $KHSO_4$/10% $K_2SO_4$ solution, NaCl sat. solution and dried ($Na_2SO_4$). The organic phase was filtered and concentrated under reduced pressure to yield a semi-solid which was triturated in hexanes: solid 3.1 g (95%); $^1$H NMR ($CDCl_3$) δ 0.60-0.64 (m, 2H), 0.85-0.90 (m, 2H), 2.89-2.92

(m, 1H), 4.60 (s, 2H), 6.20 (br, 1H), 7.44 (d, 2H), 7.71-7.74 (m, 2H); MS: m/e=210.2 (MH⁺)

EXAMPLE B (6-Methoxy-pyridin-3-yl)-methanol

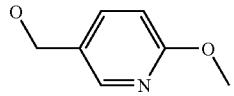

To lithium aluminium hydride (0.68 g, 18 mmol) suspended in dry THF (10 ml) was added dropwise a solution of methyl 6-methoxynicotinate (1 g, 6 mmol) in dry THF (5 ml). The reaction mixture was stirred for 2 h at r.t. then cooled (ice-bath) and quenched with water (2 ml) followed by the further addition of 1 N NaOH (6 ml) and water (2 ml). The cold-bath was removed and the mixture stirred for 30 min at r.t., filtered and concentrated under reduced pressure. The residue was diluted with water and extracted with ethyl acetate (3×). The combined organic extracts were washed with water, brine, dried (MgSO$_4$), filtered and concentrated under reduced pressure to give a crude oil which was purified over silica gel (ethyl acetate/n-heptane 1:1): colorless oil 0.45 g (51%);

$^1$H NMR (CDCl$_3$) δ 1.69 (t, 1H), 3.94 (s, 3H), 4.62 (d, 2H), 6.75 (d, 1H), 7.62 (dd, 1H), 8.13 (d, 1H); MS: m/e=139.0(M⁺)

EXAMPLE C

1-Bromomethyl-4-difluoromethyl-benzene

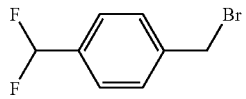

To a solution of 4-bromomethyl-benzaldehyde (1.0 g, 5.2 mmol) in CH$_2$Cl$_2$ (60 ml) was added [bis(2-methoxy-ethyl)amino]sulfurtrifluoride (50% solution in toluene, 14 ml) and the light yellow reaction mixture was stirred for 4 hours at 40° C. under an argon atmosphere. The reaction mixture was concentrated under reduced pressure and the oil residue was added dropwise to an ice-cold NaHCO$_3$ solution (half sat'd, 50 ml). The resultant mixture was extracted with ethyl acetate (3×) and the combined organic extracts were washed with NaHCO$_3$ aq., brine, dried (MgSO$_4$.2H$_2$O), filtered and concentrated under reduce pressure to yield a yellow oil: 1.03 g, 85%;

MS: m/e=220.0 (M), 141.0 (M.-Br); $^1$H NMR (400 MHz, CDCl$_3$) δ ppm 4.50 (s, 2H), 6.64 (t, J$_{HF}$=51 Hz, 1H), 7.49 (s, 4H).

EXAMPLE D

{(R)-1-[Allyl-(2,4-dimethoxy-benzyl)-carbamoyl]-but-3-enyl}-carbamic acid tert-butyl ester

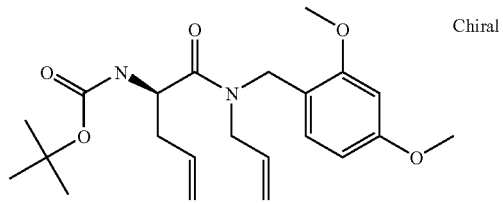

(R)-N-Boc-allylglycine (2.3 g, 9.9 mmol) was dissolved in dimethylformamide (20 ml) and activated with the coupling reagent TATU (3.5 g, 10.9 mmol) and Hünig's base (3.8 ml, 21.9 mmol) for 2 min. Allyl-(2,4-dimethoxy-benzyl)-amine (2.1 g, 9.9 mmol) dissolved in dimethylformamide (20 ml) was added to the chilled (ice-water bath) reaction mixture and the stirring was continued overnight. The solvent was evaporated and the residue was dissolved in ethyl acetate, washed with saturated NaHCO$_3$ solution, 1 M KHSO$_4$ solution, brine, dried (MgSO$_4$.2H$_2$O), filtered and concentrated under reduce pressure and purified over silica gel (ethyl acetate/n-heptane 1:4): colorless gum 2.6 g (62%);

MS: m/e=405.5 (MH⁺).

EXAMPLE E

[(R)-1-(2,4-Dimethoxy-benzyl)-2-oxo-2,3,4,7-tetrahydro-1H-azepin-3-yl]-carbamic acid tert-butyl ester

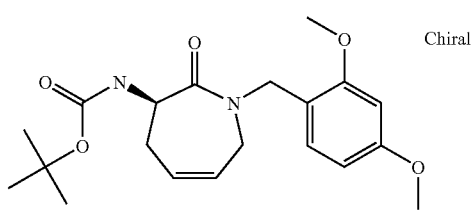

(R)-1-[Allyl-(2,4-dimethoxy-benzyl)-carbamoyl]-but-3-enyl}-carbamic acid tert-butyl ester (2.6 g, 6.4 mmol) was dissolved in CH$_2$Cl$_2$ (200 ml), [1,3-bis-(2,4,6-trimethylphenyl)-2-imidazolidinylidene]dichloro(phenylmethylene)-(tricyclohexylphosphine)ruthenium] Grubbs II catalyst (0.55 g, 0.64 mmol) was added and the reaction mixture was refluxed for 1.5 hours. The reaction mixture was concentrated under reduced pressure dissolved in ethyl acetate and washed with NaHCO$_3$ solution, 1 M KHSO$_4$ solution, brine, dried (MgSO$_4$.2H$_2$O), filtered, concentrated under reduce pressure and purified over silica gel (ethyl acetate/n-heptane 1:4->1:2): dark brown solid 1.93 g (80%);

MS: m/e=377.4 (MH⁺), 277.3 (M-Boc).

EXAMPLE F

Mixture [(R)-1-(2,4-Dimethoxy-benzyl)-2,6-dioxo-azepan-3-yl]-carbamic acid tert-butyl ester; Compound with [(R)-1-(2,4-dimethoxy-benzyl)-2,5-dioxo-azepan-3-yl]-carbamic acid tert-butyl ester

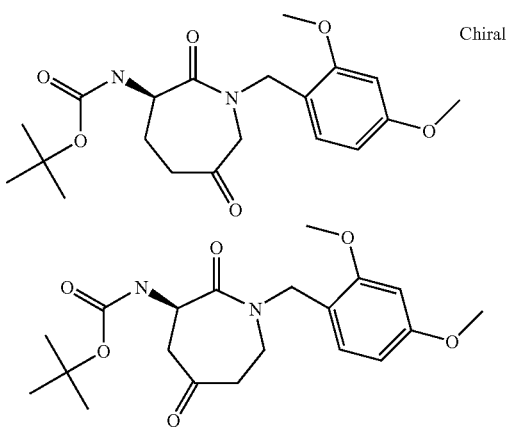

[(R)-1-(2,4-Dimethoxy-benzyl)-2-oxo-2,3,4,7-tetrahydro-1H-azepin-3-yl]-carbamic acid tert-butyl ester (5.4 g, 14.3 mmol) was dissolved in DMF/water (10:1 v/v) and then Pd(II)Cl$_2$ (1 g, 5.7 mmol) and Cu(I)Cl (7.2 g, 72.4 mmol) were added. The reaction mixture was evacuated and saturated with O$_2$ and then heated at 50° C. for 48 h. Further additions of Pd(II)Cl$_2$ (3× 0.4 equiv.) were used during the reaction. The reaction mixture was diluted with water (400 ml) and filtered over Celite. The filtrate was extracted with ethyl acetate (5×) and the combined organic extracts were washed with NaHCO$_3$ solution, 1 M KHSO$_4$ solution, brine, dried (MgSO$_4$.2H$_2$O), filtered, concentrated under reduce pressure and purified over silica gel (ethyl acetate/n-heptane 1:2->1:1) to yield a mixture of [(R)-1-(2,4-dimethoxy-benzyl)-2,6-dioxo-azepan-3-yl]-carbamic acid tert-butyl ester and [(R)-1-(2,4-dimethoxy-benzyl)-2,5-dioxo-azepan-3-yl]-carbamic acid tert-butyl ester in a 1:2 ratio: white solid 3.8 g (67%);

MS: m/e=392.9 (MH$^+$).

EXAMPLE G

[(R)-1-(2,4-Dimethoxy-benzyl)-5,5-difluoro-2-oxo-azepan-3-yl]-carbamic acid tert-butyl ester

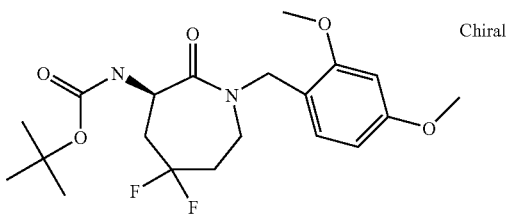

[Bis(2-methoxy-ethyl)amino]sulfur trifluoride (3.5 g, 15.8 mmol) was dissolved in dry toluene (30 ml) and cooled (ice bath) under an argon atmosphere. Boron trifluoride ethyl etherate (0.16 g, 1.13 mmol) was added dropwise and the mixture was stirred for 30 min at 5° C. A 1:2 mixture of [(R)-1-(2,4-dimethoxy-benzyl)-2,6-dioxo-azepan-3-yl]-carbamic acid tert-butyl ester and [(R)-1-(2,4-dimethoxy-benzyl)-2,5-dioxo-azepan-3-yl]-carbamic acid tert-butyl ester (4.44 g, 11.3 mmol) dissolved in toluene (15 ml) was then added dropwise, the cold-bath was removed and the reaction mixture was slowly warmed to 50° C. and further stirred for 5 h at this elevated temperature. The reaction mixture was poured into an ice-cold, half-saturated NaHCO$_3$ solution and extracted with ethyl acetate (3×). The combined organic extracts were washed water, brine, dried (MgSO$_4$.2H$_2$O), filtered, concentrated under reduce pressure and purified over silica gel (ethyl acetate/n-heptane 1:4->1:3) to yield [(R)-1-(2,4-dimethoxy-benzyl)-5,5-difluoro-2-oxo-azepan-3-yl]-carbamic acid tert-butyl ester: foam 1.32 g (25%); R$_f$ 0.4 (hexane/ethyl acetate, 1:1 v/v);

MS: m/e=415.1 (MH$^+$), at 437.1(MNa$^+$) $^1$H NMR (400 MHz, CDCl$_3$) δ ppm 1.45 (s, 9 H) 1.54-1.69 (m, 1 H) 1.75-1.98 (m, 1 H) 200-2.16 (M, 1 H) 2.49-2.65 (m, 1 H) 3.34-3.44 (m, 1 H) 3.47-3.60 (m, 1 H) 3.80 (s, 3 H) 3.81 (s, 3 H) 4.49 (d, J=14.2 Hz, 1 H) 4.52-4.56 (m, 1 H) 4.69 (d, J=14.5 Hz, 1 H) 5.97 (d, J=5.4 Hz, 1 H) 6.42-6.48 (m, 2 H) 7.19 (d, J=8.9 Hz, 1 H)

EXAMPLE H

[(R)-1-(2,4-Dimethoxy-benzyl)-6,6-difluoro-2-oxo-azepan-3-yl]-carbamic acid tert-butyl ester

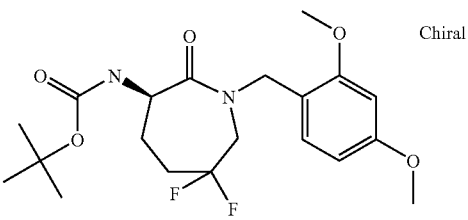

The compound was isolated in 6.5% yield as a by-product in the synthesis of the other regio-isomer [(R)-1-(2,4-dimethoxy-benzyl)-6,6-difluoro-2-oxo-azepan-3-yl]-carbamic acid tert-butyl ester.

R$_f$ 0.45 (hexane/ethyl acetate, 1:1 v/v); MS: m/e=415.3 (MH$^+$), at 432.2(MNH$_4$$^+$) $^1$H NMR (400 MHz, CDCl$_3$) δ ppm 1.41 (s, 9 H) 1.54-1.56 (m, 1 H) 2.1-2.3 (m, 3 H) 3.6-3.8 (m, 2 H) 3.80 (s, 3 H) 3.82 (s, 3 H) 4.21 (d, J=14 Hz, 1 H) 4.38 (dd, J=6/8 Hz 1 H) 5.0 (d, J=14 Hz, 1 H) 6.05 (b, 1 H) 6.45-6.48 (m, 2 H) 7.3 (d, J=8 Hz, 1 H)

EXAMPLE I

4-Chloro-N-[(R)-1-(2,4-dimethoxy-benzyl)-5,5-difluoro-2-oxo-azepan-3-yl]-benzenesulfonamide

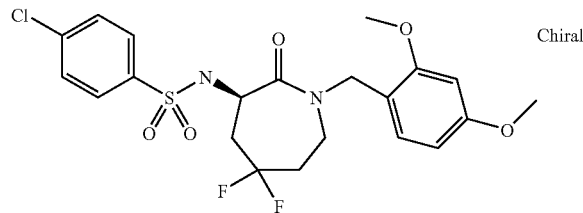

(R)-1-(2,4-Dimethoxy-benzyl)-5,5-difluoro-2-oxo-azepan-3-yl]-carbamic acid tert-butyl ester (0.77 g, 1.86 mmol) was dissolved in 4 M HCl/1,4-dioxan (20 ml) and allowed to react for 1 h. The reaction mixture was concentrated under reduced pressure and concentrated once from acetonitrile. To the resultant hydrochloride salt was added $CH_2Cl_2$ (30 ml) followed by the dropwise addition of Hünig's base (1 ml, 5.6 mmol). A solution of 4-chlorobenzenesulfonyl chloride (0.59 g, 2.8 mmol) in $CH_2Cl_2$ (4 ml) was added and the reaction mixture (pH 8) was stirred for a further 1.5 h. The reaction mixture was diluted with $CH_2Cl_2$ and washed with $NaHCO_3$ solution, 1 M $KHSO_4$ solution, brine, dried ($MgSO_4.2H_2O$), filtered, concentrated under reduce pressure and purified over silica gel (ethyl acetate/n-heptane 1:2): white crystals 0.74 g (78%);

MS: m/e=487.1 (MH$^-$); $^1$H NMR (400 MHz, CDCl$_3$) δ ppm 1.46-1.65 (m, 1 H) 1.87-2.11 (m, 2 H) 2.51-2.62 (m, 1 H) 3.27-3.32 (m, 2 H) 3.77 (s, 3 H) 3.81 (s, 3 H) 3.96-4.04 (m, 1 H) 4.38 (d, J=14.2 Hz, 1 H) 4.62 (d, J=14.5 Hz, 1 H) 6.33 (d, J=5.6 Hz, 1 H) 6.41-6.46 (m, 2 H) 6.91-6.95 (m, 1 H) 7.45-7.50 (m, 2 H) 7.78-7.83 (m, 2 H)

EXAMPLE J

4-Chloro-N-[(R)-1-(2,4-dimethoxy-benzyl)-6,6-difluoro-2-oxo-azepan-3-yl]-benzenesulfonamide

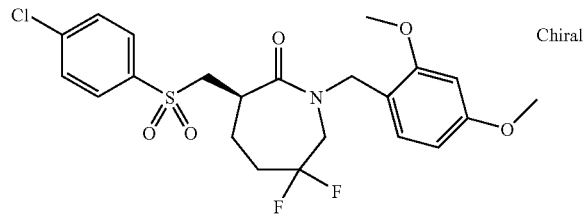

The title compound, MS: m/e=487.2 (MH$^+$), was prepared analogous to example I starting from [(R)-1-(2,4-dimethoxy-benzyl)-6,6-difluoro-2-oxo-azepan-3-yl]-carbamic acid tert-butyl ester.

EXAMPLE K

4-Chloro-N-((R)-5,5-difluoro-2-oxo-azepan-3-yl)-benzenesulfonamide

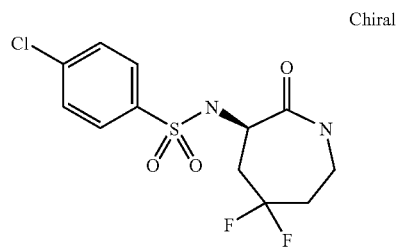

A cocktail containing 40% trifluoroacetic acid, 1% trifluoromethanesulfonic acid in $CH_2Cl_2$ (20 ml) was added to 4-chloro-N-[(R)-1-(2,4-dimethoxy-benzyl)-5,5-difluoro-2-oxo-azepan-3-yl]-benzenesulfonamide (0.5 g, 1.0 mmol). After 30 min the reaction mixture was concentrated and the residue was dissolved in ethyl acetate and washed with water, $NaHCO_3$ solution, 1 M $KHSO_4$ solution, brine, dried ($MgSO_4.2H_2O$), filtered, concentrated under reduce pressure and purified over silica gel ($CH_2Cl_2$/MeOH 95:5 v/v): white solid 0.74 g (78%);

MS: m/e=337.1 (MH$^-$);

EXAMPLE 1

4-{[(4-Chloro-benzenesulfonyl)-((R)-5,5-difluoro-2-oxo-azepan-3)-yl-amino]-methyl}-N-cyclopropyl-benzamide 4-Chloro-N-((R)-5,5-difluoro-2-oxo-azepan-3-yl)-benzenesulfonamide (0.05 g, 0.15 mmol), 4-chloromethyl-N-cyclopropyl-benzamide (0.05 g, 0.22 mmol), $K_2CO_3$ (0.20 g, 1.5 mmol), KI (0.005 g, 0.03 mmol) were added to dry DMF (2.5 ml) and the resultant reaction mixture was stirred for 3.5 h at 65° C. under an argon atmosphere. The solvent was removed under reduced pressure and the residue taken up in ethyl acetate and washed with 5% $KHSO_4$/10% $K_2SO_4$ (2×), Water, brine, dried ($MgSO_4$), filtered, concentrated under reduced pressure and purified over silica gel (ethyl acetate/n-heptane 3:2 v/v) and the purified product was lyophilized: white lyophilisate 60 mg;

MS: m/e=512.3 (MH$^+$), 534.2 (MNH$_4^+$) $^1$H NMR (400 MHz, CDCl$_3$) δ ppm 0.57-0.69 (m, 2 H) 0.79-0.94 (m, 2 H) 1.78-1.95 (m, 1 H) 1.98-2.14 (m, 1 H) 2.19-2.32 (m, 2 H) 2.88-2.94 (m, J=7.1, 7.1, 7.0, 3.8 Hz, 1 H) 3.16-3.25 (m, J=13.2, 7.9, 5.2, 2.5, 2.5 Hz, 1 H) 3.37-3.47 (m, 1 H) 4.52 (d, J=17.2 Hz, 1 H) 4.77-4.95 (m, 2 H) 5.78 (dd, J=7.7, 5.2 Hz, 1 H) 6.11-6.24 (m, 1 H) 7.40-7.46 (m, 3 H) 7.65-7.74 (m, 3 H)

EXAMPLE 2

4-Chloro-N-((R)-5,5-difluoro-2-oxo-azepan-3-yl)-N-(4-isoxazol-5-yl-benzyl)-benzenesulfonamide 4-Chloro-N-((R)-5,5-difluoro-2-oxo-azepan-3-yl)-benzenesulfonamide was alkylated using 5-(4-bromomethyl-phenyl)-isoxazole analogous to Example 1 to afford 4-chloro-N-((R)-5,5-difluoro-2-oxo-azepan-3-yl)-N-(4-isoxazol-5-yl-benzyl)-benzenesulfonamide: MS: m/e=496.0 (MH$^+$), 513.2 (MNH$_4^+$).

EXAMPLE 3

4-Chloro-N-((R)-5,5-difluoro-2-oxo-azepan-3-yl)-N-(6-methoxy-pyridin-3-ylmethyl) benzenesulfonamide a) 4-Chloro-N-[(R)-1-(2,4-dimethoxy-benzyl)-5,5-difluoro-2-oxo-azepan-3-yl]-N-(6-methoxy-pyridin-3-ylmethyl)-benzenesulfonamide 4-Chloro-N-[(R)-2,4-dimethoxy-benzyl)-5,5-difluoro-2-oxo-azepan-3-yl]-benzenesulfonamide (0.04 g, 0.07 mmol), (6-methoxy-pyridin-3-yl)-methanol (0.014 g, 0.10 mmol), triphenyl phosphine (0.04 g, 0.13 mmol) were dissolved in dry THF (3 ml) at 0-5° C. (ice-water bath) under an argon atmosphere followed by the dropwise addition of diisopropyl azodicarboxylate (28 mg, 0.13 mmol) in dry THF (0.5 ml). The reaction mixture was further stirred for 1 h at r.t. and then concentrated under reduced pressure. The crude yellow oil was purified over silica gel (ethyl acetate/n-heptane 1:2): colorless gum 23 mg (52%); MS: m/e=610.3 (MH$^+$).

b) 4-Chloro-N-((R)-5,5-difluoro-2-oxo-azepan-3-yl)-N-(6-methoxy-pyridin-3-ylmethyl) benzenesulfonamide A mixture containing trifluoroacetic acid/trifluoromethanesulfonic acid (10:1 v/v, 4 ml) was added to 4-chloro-N-[1-2,4-dimethoxy-benzyl]-5,5-difluoro-2-oxo-azepan-3-yl]-N-(6-methoxy-pyridin-3-ylmethyl)-benzenesulfonamide (21 mg, 0.03 mmol). After 1 h the reaction mixture was concentrated under reduced pressure and the residue taken up in ethyl acetate and washed with 5% KHSO$_4$/10% K$_2$SO$_4$ (2x), water, brine, dried (MgSO$_4$), filtered, concentrated under reduced pressure and purified over silica gel (ethyl acetate/n-heptane 3:2 v/v) and the purified product was lyophilized: white lyophilisate 15.3 mg;

MS: m/e=460.1 (MH$^+$).

EXAMPLE 4

4-Chloro-N-(2,3-difluoro-4-methoxy-benzyl)-N-((R)-5,5-difluoro-2-oxo-azepan-3-yl)-benzenesulfonamide 4-Chloro-N-((R)-5,5-difluoro-2-oxo-azepan-3-yl)-benzenesulfonamide was alkylated using 1-bromomethyl-2,3-difluoro-4-methoxy-benzene analogous to Example 1 to afford 4-chloro-N-(2,3-difluoro-4-methoxy-benzyl)-N-((R)-5,5-difluoro-2-oxo-azepan-3-yl)-benzenesulfonamide:

MS: m/e=495.1 (MH$^+$), 512.1(MNH$_4^+$).

EXAMPLE 5

4-Chloro-N-((R)-5,5-difluoro-2-oxo-azepan-3-yl)-N-(2-fluoro-4-methoxy-benzyl)-benzenesulfonamide 4-Chloro-N-((R)-5,5-difluoro-2-oxo-azepan-3-yl)-benzenesulfonamide was reacted with (2-fluoro-4-methoxy-phenyl)-methanol analogous to Example 3a to afford 4-chloro-N-((R)-5,5-difluoro-2-oxo-azepan-3-yl)-N-(2-fluoro-4-methoxy-benzyl)-benzenesulfonamide:

MS: m/e=477.1 (MH$^+$), 494.3 (MNH$_4^+$).

EXAMPLE 6

4-{[(4-Chloro-benzenesulfonyl)-((R)-5,5-difluoro-2-oxo-azepan-3-yl)-amino]-methyl}-3-fluoro-benzoic acid a) 4-{[(4-Chloro-benzenesulfonyl)-((R)-5,5-difluoro-2-oxo-azepan-3-yl)-amino]-methyl}-3-fluoro-benzoic acid methyl ester 4-Chloro-N-((R)-5,5-difluoro-2-oxo-azepan-3-yl)-benzenesulfonamide was alkylated using 4-bromomethyl-3-fluoro-benzoic acid methyl ester analogous to Example 1 to afford 4-{[(4-chloro-benzenesulfonyl)-((R)-5,5-difluoro-2-oxo-azepan-3-yl)-amino]-methyl}-3-fluoro-benzoic acid methyl ester: MS: m/e=504.9 (MH$^+$), 522.1(MNH$_4^+$).

b) 4-{[(4-Chloro-benzenesulfonyl)-((R)-5,5-difluoro-2-oxo-azepan-3-yl)-amino]-methyl}-3-fluoro-benzoic acid 4-{[(4-Chloro-benzenesulfonyl)-((R)-5,5-difluoro-2-oxo-azepan-3-yl)-amino]-methyl}-3-fluoro-benzoic acid methyl ester (130 mg, 0.26 mmol) was dissolved in THF/MeOH (5 ml) and treated with 1 N NaOH (1.2 ml) for 1.5 h. The reaction mixture was concentrated under reduced pressure diluted using water and extracted with diethyl ether. The aqueous phase was acidified using a 5% KHSO$_4$/10% K$_2$SO$_4$ mixture and extracted with ethyl acetate (3x). The combined organic fractions were washed with brine, dried (Na$_2$SO$_4$), filtered, concentrated under reduced pressure (103 mg). Crude product (50 mg) was purified using preparative RP(C$_{18}$) chromatography: lyophilisate 22 mg;

MS: m/e=489.0 (MH$^-$).

EXAMPLE 7

4-{[(4-Chloro-benzenesulfonyl)-((R)-5,5-difluoro-2-oxo-azepan-3-yl)-amino]-methyl}-3-fluoro-N-pyrrolidin-1-yl-benzamide 4-{[(4-Chloro-benzenesulfonyl)-((R)-5,5-difluoro-2-oxo-azepan-3-yl)-amino]-methyl}-3-fluoro-benzoic acid (50 mg, 0.10 mmol) was dissolved in DMF (1 ml) and activated with the coupling reagent TPTU (33 mg, 0.11 mmol) and Hünig's base (0.03 ml, 0.26 mmol) for 2 min. 1-Aminopyrrolidine hydrochloride (0.013 g, 0.22 mmol) and further Hünig's base (0.03 ml, 0.26 mmol were added. After 1 h the reaction mixture was concentrated under reduced pressure and the residue taken up in ethyl acetate and washed with 5% KHSO$_4$/10% K$_2$SO$_4$ (2x), water, brine, dried (MgSO$_4$), filtered, concentrated under reduced pressure and purified over silica gel (ethyl acetate->ethyl acetate/5% MeOH) and the purified product was lyophilized: white lyophilisate 32 mg;

MS: m/e=559.3 (MH$^+$), 581.2 (MNa$^+$).

EXAMPLE 8

4-Chloro-N-((R)-5,5-difluoro-2-oxo-azepan-3-yl)-N-(4-methanesulfonylbenzyl)-benzenesulfonamide 4-Chloro-N-((R)-5,5-difluoro-2-oxo-azepan-3-yl)-benzenesulfonamide was alkylated using 4-methylsulphonylbenzyl bromide analogous to Example 1 to afford 4-chloro-N-((R)-5,5-difluoro-2-oxo-azepan-3-yl)-N-(4- methanesulfonylbenzyl)-benzenesulfonamide:
MS: m/e=507.2 (MH$^+$), 524.1(MNH$_4^+$).

EXAMPLE 9

4-Chloro-N-(4-difluoromethoxy-benzyl)-N-((R)-5,5-difluoro-2-oxo-azepan-3-yl)-benzenesulfonamide 4-Chloro-N-((R)-5,5-difluoro-2-oxo-azepan-3-yl)-benzenesulfonamide was alkylated using 4-(difluoromethoxy)benzyl bromide analogous to Example 1 to afford 4-chloro-N-(4-difluoromethoxy-benzyl)-N-((R)-5,5-difluoro-2-oxo-azepan-3-yl)-benzenesulfonamide:
MS: m/e=495.1 (MH$^+$), 512.1(MNH$_4^+$).

EXAMPLE 10

4-Chloro-N-(4-difluoromethyl-benzyl)-N-((R)-5,5-difluoro-2-oxo-azepan-3-yl)-benzenesulfonamide 4-Chloro-N-((R)-5,5-difluoro-2-oxo-azepan-3-yl)-benzenesulfonamide was alkylated using 1-bromomethyl-4-difluoromethyl-benzene analogous to Example 1 to afford 4-chloro-N-(4-difluoromethyl-benzyl)-N-((R)-5,5-difluoro-2-oxo-azepan-3-yl)-benzenesulfonamide:
MS: m/e=479.1 (MH$^+$), 496.0 (MNH$_4^+$).

EXAMPLE 11

N-(1-Benzoyl-piperidin-4-ylmethyl)-4-chloro-N-((R)-5,5-difluoro-2-oxo-azepan-3-yl)-benzenesulfonamide a) 4-{[(4-Chloro-benzenesulfonyl)-((R)-5,5-difluoro-2-oxo-azepan-3-yl)-amino]-methyl}-piperidine-1-carboxylic acid tert-butyl ester 4-Chloro-N-((R)-5,5-difluoro-2-oxo-azepan-3-yl)-benzenesulfonamide was alkylated using 4-(toluene-4-sulfonyloxymethyl)-piperidine-1-carboxylic acid tert-butyl ester analogous to Example 1 to afford 4-{[(4-chloro-benzenesulfonyl)-((R)-5,5-difluoro-2-oxo-azepan-3-yl)-amino]-methyl}-piperidine-1-carboxylic acid tert-butyl ester:
MS: m/e=536.3 (MH$^+$), 553.2 (MNH$_4^+$).

b) 4-Chloro-N-((R)-5,5-difluoro-2-oxo-azepan-3-yl)-N-piperidin-4-ylmethyl-benzenesulfonamide 4-{[(4-Chloro-benzenesulfonyl)-((R)-5,5-difluoro-2-oxo-azepan-3-yl)-amino]-methyl}-piperidine-1-carboxylic acid tert-butyl ester (0.105 g, 0.2 mmol) was dissolved in a mixture of trifluoroacetic acid and dichloromethane (1:1) and stirred overnight. After extraction with aqueous sodium bicarbonate solution the organic layer was dried (MgSO$_4$) and evaporated to yield 80 mg (94%) of 4-chloro-N-((R)-5,5-difluoro-2-oxo-azepan-3-yl)-N-piperidin-4-ylmethyl-benzenesulfonamide;
MS: m/e=436.2 (MH$^+$).

c) N-(1-Benzoyl-piperidin-4-ylmethyl)-4-chloro-N-((R)-5,5-difluoro-2-oxo-azepan-3-yl)-benzenesulfonamide 4-Chloro-N-((R)-5,5-difluoro-2-oxo-azepan-3-yl)-N-piperidin-4-ylmethyl-benzenesulfonamide (0.04 g, 0.09 mmol) and triethylamine (19 mg, 0.18 mmol) were dissolved in dichloromethane (1.5 ml). Then benzoyl chloride (0.018 g, 0.13 mmol) was added and the mixture was stirred overnight at room temperature. The reaction mixture was partitioned between aqueous sodium bicarbonate solution and ethyl acetate. The organic layer was dried (MgSO$_4$) and concentrated under reduced pressure. The residue was purified over silica gel (heptane/ethyl acetate 1:1) to yield 29 mg (58%) of the title compound;
MS: m/e=540.3 (MH$^+$), 557.1 (MNH$_4^+$).

EXAMPLE 12

4-Chloro-N-((R)-5,5-difluoro-2-oxo-azepan-3-yl)-N-[2-floro-4-(2H-[1,2,4]triazol-3-yl)-benzyl]-benzenesulfonamide a) 4-Chloro-N-(4-cyano-2-fluoro-benzyl)-N-((R)-5,5-difluoro-2-oxo-azepan-3-yl)-benzenesulfonamide 4-Chloro-N-((R)-5,5-difluoro-2-oxo-azepan-3-yl)-benzenesulfonamide was alkylated using 4-bromomethyl-3-fluoro-benzonitrile analogous to Example 1 to afford 4-chloro-N-(4-cyano-2-fluoro-benzyl)-N-((R)-5,5-difluoro-2-oxo-azepan-3-yl)-benzenesulfonamide:MS: m/e=472.2 (MH$^+$).

b) 4-{[(4-Chloro-benzenesulfonyl)-((R)-5,5-difluoro-2-oxo-azepan-3-yl)-amino]-methyl}-3-fluoro-benzimidic acid ethyl ester hydrochloride 4-Chloro-N-(4-cyano-2-fluoro-benzyl)-N-((R)-5,5-difluoro-2-oxo-azepan-3-yl)-benzenesulfonamide (0.23 g, 0.49 mmol) was suspended in dry ethanol (10 ml) and cooled to 0° C. Dry HCl gas was gently bubbled over 30 min into this suspension. The light red reaction mixture was stirred at room temperature for 20 h. A clear yellow solution resulted which was concentrated under reduced pressure and the crude was used directly in the next step: 0.28 g; MS: m/e=516.2 (MH$^-$).

c) 4-Chloro-N-((R)-5,5-difluoro-2-oxo-azepan-3-yl)-N-[2-fluoro-4-(2H-[1,2,4]triazol-3-yl)-benzyl]-benzenesulfonamide The crude hydrochloride salt (0.27 g, ca. 0.49 mmol) and formyl hydrazine (90% grade, 36 mg, 0.54 mmol) were dissolved in pyridine (7.3 ml) and stirred for 3 h under an argon atmosphere. The reaction mixture was concentrated under reduced pressure and xylenes (12.1 ml) were added and the reaction mixture was heated at 145° C. for 30 min. The reaction mixture was concentrated under reduced pressure and the crude yellow solid was purified over silica gel (CH$_2$Cl$_2$/MeOH 95:5) and the purified product was lyophilized: white lyophilisate 75 mg;
MS: m/e=514.2 (MH$^+$), 531.0 (MNH$_4^+$).

EXAMPLE 13

4-{[(4-Chloro-benzenesulfonyl)-((R)-6,6-difluoro-2-oxo-azepan-3-yl)-amino]-methyl}-N-cyclopropyl-benzamide 4-Chloro-N-[(R)-1-(2,4-dimethoxy-benzyl)-6,6-difluoro-2-oxo-azepan-3-yl]-benzenesulfonamide was subjected to dimethoxybenzyl protecting group removal analogous to Example K and further alkylated using chloromethyl-N-cyclopropyl-benzamide analogous to the protocol in Example 1 to yield 4-{[(4-chloro-benzenesulfonyl)-((R)-6,6-difluoro-2-oxo-azepan-3-yl)-amino]-methyl}-N-cyclopropyl-benzamide.
MS: m/e=512.1 (MH$^+$); 1H NMR (400 MHz, CDCl$_3$) δ ppm 0.56-0.68 (m, 2 H) 0.81-0.91 (m, 2 H) 1.72-1.87 (m, 2 H) 1.95-2.14 (m, 1 H) 2.17-2.27 (m, 1 H) 2.91 (qd, J=7.1, 3.8 Hz, 1 H) 3.31-3.50 (m, 1 H) 3.54-3.67 (m, 1 H) 4.51-4.62 (m, 1 H) 4.82-4.94 (m, 2 H) 5.51-5.62 (m, 1 H) 6.16 (s, 1 H) 7.41-7.52 (m, 3 H) 7.65-7.72 (m, 3 H)

EXAMPLE 14

3-(4-{[(4-Chloro-benzenesulfonyl)-((R)-5,5-difluoro-2-oxo-azepan-3-yl)-amino]-methyl}-phenyl)-propionic acid a) 3-(4-{[(4-Chloro-benzenesulfonyl)-((R)-5,5-difluoro-2-oxo-azepan-3-yl)-amino]-methyl}-phenyl)-propionic acid methyl ester 4-Chloro-N-((R)-5,5-difluoro-2-oxo-azepan-3-yl)-benzenesulfonamide was alkylated using 3-(4-bromomethyl-phenyl)-propionic acid methyl ester analogous to Example 1 to afford 3-(4-{[(4-chloro-benezenesulfonyl)-((R)-5,5-difluoro-2-oxo-azepan-3-yl)-amino]-methyl}-phenyl)-propionic acid methyl ester:

MS: m/e=515.1 ($MH^+$), 532.1 ($MNH_4^+$).

b) 3-(4-{[(4-Chloro-benzenesulfonyl)-((R)-5,5-difluoro-2-oxo-azepan-3-yl)-amino]-methyl}-phenyl)-propionic acid 3-(4-{[(4-chloro-benzenesulfonyl)-((R)-5,5-difluoro-2-oxo-azepan-3-yl)-amino]-methyl}-phenyl)-propionic acid methyl ester (65 mg, 0.13 mmol) was dissolved in methanol (0.5 ml) and treated with 2 N LiOH in water (0.25 ml, 0.5 mmol) overnight at 40° C. The reaction mixture was distributed between 4 N HCl and ethyl acetate. The organic layer was dried ($MgSO_4$) and concentrated under reduced pressure. The crude product (50 mg) was purified using column chromatography (dichloromethane/methanol 90:10) to yield 45 mg (71%);

MS: m/e=499.0 ($MH^-$).

EXAMPLE 15

3-(4-{[(4-Chloro-benzenesulfonyl)-((R)-5,5-difluoro-2-oxo-azepan-3-yl)-amino]-methyl}-phenyl)-3-methyl-butyric acid This compound was prepared analogous to Example 14 using 3-(4-bromomethyl-phenyl)-3-methyl-butyric acid methyl ester in step 14a) to afford 3-(4-{[(4-chloro-benzenesulfonyl)-((R)-5,5-difluoro-2-oxo-azepan-3-yl)-amino]-methyl}-phenyl)-3-methyl-butyric acid:

MS: m/e=527.1 ($MH^-$).

EXAMPLE 16

3,3,3-Trifluoro-propane-1-sulfonic acid ((R)-5,5-difluoro-2-oxo-azepan-3-yl)-(6-methoxy-pyridin-3-ylmethyl)-amide a) 3,3,3-Trifluoro-propane-1-sulfonic acid [(R)-1-(2,4-dimethoxy-benzyl)-5,5-difluoro-2-oxo-azepan-3-yl]-amide

[(R)-1-(2,4-Dimethoxy-benzyl)-5,5-difluoro-2-oxo-azepan-3-yl]-carbamic acid tert-butyl ester (0.85 g, 1.85 mmol) was dissolved in 38 ml dichloromethane. 4 M HCl/1,4-dioxan (20 ml) were added dropwise and the mixture was allowed to react for 1 h. The reaction mixture was concentrated under reduced pressure and concentrated once from acetonitrile. To 291 mg of the resultant hydrochloride salt was added $CH_2Cl_2$ (20 ml) followed by the dropwise addition of Hünig's base (0.36 ml, 2.1 mmol). A solution of 3,3,3-trifluoropropane-1-sulfonyl chloride (0.19 g, 0.9 mmol) in $CH_2Cl_2$ (5 ml) was added and the reaction mixture (pH 8) was stirred for a further 1.5 h. The reaction mixture was purified over silica gel (heptane-ethylacetate, 95:5-0:100): white solid 0.30 g (77%);

MS: m/e=473.1 ($M-^-$).

b) 3,3,3-Trifluoro-propane-1-sulfonic acid [(R)-1-(2,4-dimethoxy-benzyl)-5,5-difluoro-2-oxo-azepan-3-yl]-(6-methoxy-pyridin-3-ylmethyl)-amide 3,3,3-Trifluoro-propane-1-sulfonic acid [(R)-1-(2,4-dimethoxy-benzyl)-5,5-difluoro-2-oxo-azepan-3-yl]-amide (0.15 g, 0.31 mmol), (6-methoxy-pyridin-3-yl)-methanol (0.06 g, 0.38 mmol), triphenyl phosphine (0.17 g, 0.62 mmol) were dissolved in dry THF (15 ml) at 0-5° C. (ice-water bath) under an argon atmosphere followed by the dropwise addition of diisopropyl azodicarboxylate (0.12 ml, 0.62 mmol) in dry THF (1.5 ml). The reaction mixture was further stirred for 1 h at r.t. and then concentrated under reduced pressure. The crude oil was purified over silica gel (first: heptane-ethylacetate, 97:3-0:100; second: dichloromethane-methanol, 98:2-90:10): white solid 214 mg (81%);

MS: m/e=654.2 ($M+CH_3COO^-$).

c) 3,3,3-Trifluoro-propane-1-sulfonic acid ((R)-5,5-difluoro-2-oxo-azepan-3-yl)-(6-methoxy-pyridin-3-ylmethyl)-amide A mixture containing trifluoroacetic acid/trifluoromethanesulfonic acid (5:2 v/v, 0.76 ml) was added to 3,3,3-trifluoro-propane-1-sulfonic acid [(R)-1-(2,4-dimethoxy-benzyl)-5,5-difluoro-2-oxo-azepan-3-yl]-(6-methoxy-pyridin-3-ylmethyl)-amide (0.2 g, 0.24 mmol) in dichloromethane (10 ml). After 2 h the reaction mixture was concentrated under reduced pressure and the residue taken up in ethyl acetate and washed with water, saturated aqueous sodium bicarbonate and brine, dried ($Na_2SO_4$), filtered, concentrated under reduced pressure and purified over silica gel (heptane-ethyl acetate, 9:1-0:1): white solid 72 mg (69%);

MS: m/e=446.2 ($MH^+$).

EXAMPLE 17

5-Chloro-thiophene-2-sulfonic acid ((R)-5,5-difluoro-2-oxo-azepan-3-yl)-(6-methoxy-pyridin-3-ylmethyl)-amide a) 5-Chloro-thiophene-2-sulfonic acid [(R)-1-(2,4-dimethoxy-benzyl)-5,5-difluoro-2-oxo-azepan-3-yl]-amide

[(R)-1-(2,4-Dimethoxy-benzyl)-5,5-difluoro-2-oxo-azepan-3-yl]-carbamic acid tert-butyl ester (0.85 g, 1.85 mmol) was dissolved in 38 ml dichloromethane. 4 M HCl/1,4-dioxan (20 ml) were added dropwise and the mixture was allowed to react for 1 h. The reaction mixture was concentrated under reduced pressure and concentrated once from acetonitrile. To 291 mg of the resultant hydrochloride salt was added $CH_2Cl_2$ (20 ml) followed by the dropwise addition of Hünig's base (0.36 ml, 2.1 mmol). A solution of 5-chlorothiophene-2-sulfonyl chloride (0.21 g, 0.9 mmol) in $CH_2Cl_2$ (5 ml) was added and the reaction mixture (pH 8) was stirred for a further 1.5 h. The reaction mixture was purified over silica gel (heptane-ethylacetate, 95:5-0:100): white solid 0.40 g (97%);.

MS: m/e=493.1 ($M-H^{31}$ ).

b) 5-Chloro-thiophene-2-sulfonic acid [(R)-1-(2,4-dimethoxy-benzyl)-5,5-difluoro-2-oxo-azepan-3-yl]-(6-methoxy-pyridin-3-ylmethyl)-amide 5-Chloro-thiophene-2-sulfonic acid [(R)-1-(2,4-dimethoxy-benzyl)-5,5-difluoro-2-oxo-azepan-3-yl]-amide (0.20 g, 0.40 mmol), (6-methoxy-pyridin-3-yl)-methanol (0.07 g, 0.48 mmol), triphenyl phosphine (0.22 g, 0.80 mmol) were dissolved in dry THF (15 ml) at 0-5° C. (ice-water bath) under an argon atmosphere followed by the dropwise addition of diisopropyl azodicarboxylate (0.16 ml, 0.80 mmol) in dry THF (1.5 ml). The reaction mixture was further stirred for 1 h at r.t. and then concentrated under reduced pressure. The crude oil was purified over silica gel (first: heptane-ethylacetate, 97:3-0:100; second: dichloromethane-methanol, 98:2-90:10): white solid 0.19 g (53%);

MS: m/e=674.2 (M+CH₃COO⁻).

c) 5-Chloro-thiophene-2-sulfonic acid ((R)-5,5-difluoro-2-oxo-azepan-3-yl)-(6-methoxy-pyridin-3-ylmethyl)-amide A mixture containing trifluoroacetic acid/trifluoromethanesulfonic acid (5:2 v/v, 0.62 ml) was added to 5-chloro-thiophene-2-sulfonic acid [(R)-1-(2,4-dimethoxy-benzyl)-5,5-difluoro-2-oxo-azepan-3-yl]-(6-methoxy-pyridin-3-ylmethyl)-amide (0.17 g, 0.19 mmol) in dichloromethane (10 ml). After 2 h the reaction mixture was concentrated under reduced pressure and the residue taken up in ethyl acetate and washed with water, saturated aqueous sodium bicarbonate and brine, dried (Na₂SO₄), filtered, concentrated under reduced pressure and purified over silica gel (heptane-ethylacetate, 9:1-0:1): white solid 69 mg (77%);

MS: m/e=466.1 (MH⁺).

EXAMPLE 18

5-Chloro-pyridine-2-sulfonic acid (4-difluoromethoxy-benzyl)-((R)-5,5-difluoro-2-oxo-azepan-3-yl)-amide a) 5-Chloro-pyridine-2-sulfonic acid [(R)-1-(2,4-dimethoxy-benzyl)-5,5-difluoro-2-oxo-azepan-3-yl]-amide

[(R)-1-(2,4-Dimethoxy-benzyl)-5,5-difluoro-2-oxo-azepan-3-yl]-carbamic acid tert-butyl ester (0.46 g, 1.0 mmol) was dissolved in 20 ml dichloromethane. 4 M HCl/1,4-dioxan (20 ml) were added dropwise and the mixture was allowed to react for 1 h. The reaction mixture was concentrated under reduced pressure and concentrated once from acetonitrile. To the resultant hydrochloride salt was added CH₂Cl₂ (15 ml) followed by the dropwise addition of Hünig's base (0.44 ml, 2.5 mmol). A solution of 5-chloropyridine-2-sulfonyl chloride (0.33 g, 1.1 mmol) in CH₂Cl₂ (5 ml) was added and the reaction mixture (pH 8) was stirred for a further 1.5 h. The reaction mixture was purified over silica gel (heptane-ethylacetate, 95:5-0:100): white solid 0.37 g (76%).

MS: m/e=490.2 (MH⁺).

b) 5-Chloro-pyridine-2-sulfonic acid ((R)-5,5-difluoro-2-oxo-azepan-3-yl)-amide

A mixture containing trifluoroacetic acid/trifluoromethanesulfonic acid (5:2 v/v, 2.44 ml) was added to 5-chloro-pyridine-2-sulfonic acid [(R)-1-(2,4-dimethoxy-benzyl)-5,5-difluoro-2-oxo-azepan-3-yl]-amide (0.37 g, 0.76 mmol) in dichloromethane (20 ml). After 2 h the reaction mixture was concentrated under reduced pressure and the residue taken up in ethyl acetate and washed with water, saturated aqueous sodium bicarbonate and brine, dried (Na₂SO₄), filtered, concentrated under reduced pressure and purified over silica gel (heptane-ethylacetate, 1:1-0:1); white solid 0.22 g (84%); MS: m/e=340.0 (MH⁺).

c) 5-Chloro-pyridine-2-sulfonic acid (4-difluoromethoxy-benzyl)-((R)-5.5-difluoro-2-oxo-azepan-3-yl)-amide 5-Chloro-pyridine-2-sulfonic acid ((R)-5,5-difluoro-2-oxo-azepan-3-yl)-amide (0.21 g, 0.61 mmol), 4-(difluoromethoxy)benzyl bromide (0.23 g, 0.91 mmol), K₂CO₃ (0.85 g, 6.08 mmol), KI (0.02 g, 0.12 mmol) were added to dry DMF (10 ml) and the resultant reaction mixture was stirred for 1.5 h at 65° C. and for additional 3 h at room temperature under an argon atmosphere. The solvent was removed under reduced pressure and the residue was purified over silica gel (first: ethyl acetate/n-heptane 1:2 v/v; second: dichloromethane/MeOH, 100:0-95:5): brownish oil, 0.23 g; MS: m/e=496.1 (MH⁺).

The invention claimed is:

1. A compound of formula

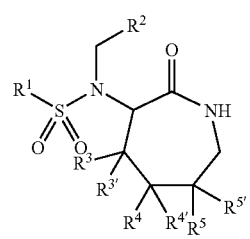

I wherein
R¹ is lower alkyl substituted by halogen, or is aryl or heteroaryl, each of which is unsubstituted or substituted by halogen;
R² is heterocycloalkyl, aryl or heteroaryl, each of which is unsubstituted or substituted by one or more substituents, selected from the group consisting of halogen, lower alkyloxy, lower alkyl substituted by halogen, O-lower alkyl substituted by halogen C(O)—NR"₂, (CR₂)ₘ—C(O)—R', heteroaryl and S(O)₂-lower alkyl;
R³/R³', R⁴/R⁴' and R⁵/R⁵' are each independently hydrogen or fluoro, wherein at least one of R⁴/R⁴' or R⁵/R⁵' is always fluoro;
R' is aryl or hydroxy;
R" is hydrogen, cycloalkyl or heterocycloalkyl;
R is hydrogen or lower alkyl; and
m is 0, 1, 2 or 3;
or a pharmaceutically acceptable acid addition salt, optically pure enantiomer, racemate or diastereomeric mixture thereof.

2. A compound of claim 1, wherein R⁴/R⁴' are both fluoro and R¹ is phenyl substituted by halogen.

3. A compound of claim 2, wherein R² is phenyl substituted by halogen or C(O)—N(R")₂.

4. A compound of claim 3, selected from the group consisting of 4-{[(4-chloro-benzenesulfonyl)-((R)-5,5-difluoro-2-oxo-azepan-3-yl)-amino]-methyl}-N-cyclopropyl-benzamide and 4-{[(4-chloro-benzenesulfonyl)-((R)-5,5-difluoro-2-oxo-azepan-3-yl)-amino]-methyl}-3-fluoro-N-pyrrolidin-1-yl-benzamide.

5. A compound of claim 2, wherein R² is phenyl substituted by halogen or lower alkoxy.

6. A compound of claim 5, which is 4-chloro-N-(2,3-difluoro-4-methoxy-benzyl)-N-((R)-5,5-difluoro-2-oxo-azepan-3-yl)-benzenesulfonamide.

7. A compound of claim 2, wherein R² is phenyl substituted by halogen or heteroaryl.

8. A compound of claim 7, which compound is 4-chloro-N-((R)-5,5-difluoro-2-oxo-azepan-3-yl)-N-[2-fluoro-4-(2H-[1,2,4]triazol-3-yl)-benzyl]-benzenesulfonamide.

9. A compound of claim 2, wherein R² is phenyl substituted (CR₂)ₘC(O)—R'.

10. A compound of claim 9, selected from the group consisting of 3-(4-{[(4-chloro-benzenesulfonyl)-((R)-5,5-difluoro-2-oxo-azepan-3-yl)-amino]-methyl}-phenyl)-propionic acid and 3-(4-{[(4-chloro-benzenesulfonyl)-((R)-5,5- difluoro-2-oxo-azepan-3-yl)-amino]-methyl}-phenyl)-3-methyl-butyric acid.

11. A compound of claim 1, wherein $R^1$ is heteroaryl substituted by halogen.

12. A compound of claim 1, wherein $R^1$ is lower alkyl substituted by halogen.

13. A pharmaceutical composition comprising a therapeutically effective amount of a compound of formula I

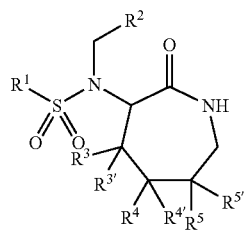

wherein $R^1$ is lower alkyl substituted by halogen, or is aryl or heteroaryl, each of which is unsubstituted or substituted by halogen;

$R^2$ is heterocycloalkyl, aryl or heteroaryl, each of which is unsubstituted or substituted by one or more substituents, selected from the group consisting of halogen, lower alkyloxy, lower alkyl substituted by halogen, O-lower alkyl substituted by halogen C(O)—NR''$_2$, (CR$_2$)$_m$—C(O)—R', heteroaryl and S(O)$_2$-lower alkyl;

$R^3/R^{3'}$, $R^4/R^{4'}$ and $R^5/R^{5'}$ are each independently hydrogen or fluoro, wherein at least one of $R^4/R^{4'}$ or $R^5/R^{5'}$ is always fluoro;

R' is aryl or hydroxy;

R'' is hydrogen, cycloalkyl or heterocycloalkyl;

R is hydrogen or lower alkyl; and m is 0, 1, 2 or 3;

or a pharmaceutically acceptable acid addition salt, optically pure enantiomer, racemate or diastereomeric mixture thereof and a pharmaceutically acceptable carrier.

\* \* \* \* \*